United States Patent [19]

Becker et al.

[11] Patent Number: 5,731,148
[45] Date of Patent: Mar. 24, 1998

[54] ADDUCT PROTECTION ASSAY

[75] Inventors: Michael Becker; Norman C. Nelson, both of San Diego, Calif.

[73] Assignee: Gen-Probe Incorporated, San Diego, Calif.

[21] Appl. No.: 478,221

[22] Filed: Jun. 7, 1995

[51] Int. Cl.[6] .................. C12Q 1/68; G01N 21/00; G01N 21/76; G01N 33/00
[52] U.S. Cl. ................. 435/6; 435/4; 436/164; 436/172; 436/56; 436/63; 436/94; 436/86
[58] Field of Search ............. 435/6, 4, 28; 436/546, 436/544, 536, 501, 164, 172, 94, 86, 63, 56, 503

[56] References Cited

U.S. PATENT DOCUMENTS

| | | |
|---|---|---|
| 3,539,574 | 11/1970 | Sheehan et al. . |
| 3,817,837 | 6/1974 | Rubenstein et al. . |
| 4,174,384 | 11/1979 | Ulman et al. . |
| 4,190,496 | 2/1980 | Rubenstein et al. . |
| 4,199,559 | 4/1980 | Ulman et al. . |
| 4,318,707 | 3/1982 | Litman et al. . |
| 4,383,031 | 5/1983 | Boguslaski et al. . |
| 4,462,931 | 7/1984 | Cohen et al. . |
| 4,508,642 | 4/1985 | World . |
| 4,581,333 | 4/1986 | Kourilsky et al. . |
| 4,640,898 | 2/1987 | Halfman . |
| 4,655,969 | 4/1987 | Richter et al. . |
| 4,668,640 | 5/1987 | Wang et al. . |
| 4,670,379 | 6/1987 | Miller et al. . |
| 4,698,183 | 10/1987 | Koroscil . |
| 4,745,181 | 5/1988 | Law et al. . |
| 4,767,608 | 8/1988 | Dugliss . |
| 4,816,419 | 3/1989 | Halfman . |
| 4,834,918 | 5/1989 | Wulff et al. . |
| 4,883,898 | 11/1989 | Yang . |
| 4,918,192 | 4/1990 | Law et al. . |
| 4,927,769 | 5/1990 | Chang et al. . |
| 4,946,958 | 8/1990 | Campbell et al. . |
| 4,950,613 | 8/1990 | Arnold, Jr. et al. ........... 436/546 |
| 5,093,270 | 3/1992 | Chang et al. . |
| 5,110,932 | 5/1992 | Law et al. . |
| 5,185,439 | 2/1993 | Arnold, Jr. et al. . |
| 5,241,070 | 8/1993 | Law et al. . |
| 5,281,712 | 1/1994 | McCapra et al. . |
| 5,283,174 | 2/1994 | Arnold, Jr. et al. . |
| 5,283,334 | 2/1994 | McCapra et al. . |
| 5,284,951 | 2/1994 | McCapra et al. . |
| 5,284,952 | 2/1994 | Ramakrishnan . |
| 5,290,936 | 3/1994 | Beheshti et al. . |
| 5,321,136 | 6/1994 | McCapra ..................... 546/104 |
| 5,338,847 | 8/1994 | McCapra et al. ............. 546/104 |
| 5,491,072 | 2/1996 | Akhavan-Tafti et al. ......... 435/28 |
| 5,521,103 | 5/1996 | Zomer et al. .............. 436/536 |

FOREIGN PATENT DOCUMENTS

| | | |
|---|---|---|
| 4018885 | 3/1985 | Australia . |
| 4031085 | 3/1985 | Australia . |
| 5214686 | 7/1989 | Australia . |
| 2074014 | 7/1992 | Canada . |
| 0070685 | 7/1982 | European Pat. Off. . |
| 0070686 | 7/1982 | European Pat. Off. . |
| 0082636 | 12/1982 | European Pat. Off. . |
| 0159719 | 4/1985 | European Pat. Off. . |
| 0212951 | 8/1985 | European Pat. Off. . |
| 0216553 | 9/1986 | European Pat. Off. . |
| 0257541 | 8/1987 | European Pat. Off. . |
| 0273115 | 10/1987 | European Pat. Off. . |
| 0313219 | 9/1988 | European Pat. Off. . |
| 0638807 | 9/1988 | European Pat. Off. . |
| 0322926 | 12/1988 | European Pat. Off. . |
| 0324202 | 12/1988 | European Pat. Off. . |
| 0330050 | 2/1989 | European Pat. Off. . |
| 0353971 | 7/1989 | European Pat. Off. . |
| 0330433 | 8/1989 | European Pat. Off. . |
| 0361817 | 4/1990 | European Pat. Off. . |
| 0492570 | 7/1992 | European Pat. Off. . |
| 0534380 | 9/1992 | European Pat. Off. . |
| 0602524 | 12/1992 | European Pat. Off. . |
| 0617107 | 9/1993 | European Pat. Off. . |
| 0609885 | 2/1994 | European Pat. Off. . |
| 0625510 | 11/1994 | European Pat. Off. ...... C07D 219/04 |
| 0639648 | 2/1995 | European Pat. Off. . |
| 0709466 | 6/1996 | European Pat. Off. . |
| 335147 | 2/1991 | Japan . |
| 5255264 | 10/1993 | Japan . |
| 6009566 | 1/1994 | Japan ..................... C07D 219/02 |
| 69566 | 1/1994 | Japan . |
| 7330838 | 12/1995 | Japan ..................... C08F 220/36 |
| 8000292 | 1/1996 | Japan ..................... C12Q 1/42 |
| 2112779 | 12/1982 | United Kingdom . |
| 2233451 | 6/1989 | United Kingdom . |
| 8908256 | 9/1989 | WIPO . |
| 9207864 | 5/1992 | WIPO . |
| 9209580 | 6/1992 | WIPO . |
| 9322460 | 11/1993 | WIPO . |
| WO9402486 | 2/1994 | WIPO ..................... C07D 498/10 |
| 9423069 | 10/1994 | WIPO . |
| 9503427 | 2/1995 | WIPO . |

OTHER PUBLICATIONS

Arnold et al. (1989) Clinical Chemistry 35:1588–94.
Batmanghelich et al. (1991) J. Photochem. Photobiol. 56:249–54.

(List continued on next page.)

*Primary Examiner*—W. Gary Jones
*Assistant Examiner*—Amy Atzel
*Attorney, Agent, or Firm*—Lyon & Lyon LLP

[57] ABSTRACT

The present invention features an adduct protection assay involving the use of a labelled binding partner and a signal altering ligand. The signal altering ligand can preferentially alter the ability of label which is not part of a binding partner:analyte complex to produce a detectable signal, compared to its ability to alter signal produced from label which is part of a binding partner:analyte complex. The presence or amount of analyte can be determined by detecting the signal produced from unaltered label. The adduct protection assay is very versatile. For example, alteration of signal can be carried out under a wide range of conditions (e.g., pH, temperature, and ionic strength), and both label alteration and signal triggering can be carried out at essentially constant temperature to achieve a high degree of sensitivity.

36 Claims, 4 Drawing Sheets

OTHER PUBLICATIONS

Littig et al. (1992) Analytical Chemistry 64:1140–44.

Matsubara et al. (1992) Human Immunology 35:132–9.

Nelson et al. (1992) Detection of Acridinium Esters by Chemiluminescence, in *Nonisotopic DNA Probe Techniques*. Academic Press, Inc.

Arnold et al., "Assay Formats Involving Acridinium–Ester–Labeled DNA Probes," *Clin. Chem.* 35:1588–1594 (1989).

Campbell et al., Abstract: "Luminescent labeling materials and procedures," *Chemical Abstracts* 99:154813y (1983).

Campbell, *Chemiluminescence: Principles and Application in Biology and Medicine*, Ellis Horwood Ltd. Chichester England, 1988.

Hammond et al., "Nucleophilic Addition to the 9 Position of 9–Phenylcarboxylate–10–methylacridinium Protects against Hydrolysis of the Ester," *J. Biolumin. Chemilumin.* 6:35–43 (1991).

Nelson et al., "Detection Of Acridinium Esters By Chemiluminescence" in: *Nonisotopic DNA Probe Techniques*, (Kricka ed., Academic Press, 1992) pp. 275–311.

Nelson and Kacian, "Chemiluminescent DNA probes: a comparison of the acridinium ester and dioxetane detection systems and their use in clinical diagnostic assays," *Clin. Chem. Acta* 194:73–90 (1990).

Weeks et al., "Immunoassays using acridinium esters," *Methods in Enzymology* 133:366–368 (1986).

o-diBr-AE

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 1:

GGGGTTCTTT TCGCCTTTCC CTCACGG              27

( 2 ) INFORMATION FOR SEQ ID NO: 2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 2:

CCGTGAGGGA AAGGCGAAAA GAACCCC              27

( 2 ) INFORMATION FOR SEQ ID NO: 3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear -continued (  i  i  ) MOLECULE TYPE: nucleic acid (  x  i  ) SEQUENCE DESCRIPTION: SEQ ID NO: 3:

ATCATCCATG TATTGATAGA TAACTATGTC TGG    33

( 2 ) INFORMATION FOR SEQ ID NO: 4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 4:

CCAGACATAG TTATCTATCA ATACATGGAT GAT    33

( 2 ) INFORMATION FOR SEQ ID NO: 5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 5:

GCTCGTTGCG GGACTTAACC CAACAT    26

( 2 ) INFORMATION FOR SEQ ID NO: 6:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 6:

ATGTTGGGTT AAGTCCCGCA ACGAGC    26

( 2 ) INFORMATION FOR SEQ ID NO: 7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 7:

CGTTACTCGG ATGGCCCAAA TATCGCCAC    29

( 2 ) INFORMATION FOR SEQ ID NO: 8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 8:

GTGGCGATAT TTGGGCCATC CGAGTAACG    29

( 2 ) INFORMATION FOR SEQ ID NO: 9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 9:

GTGGCGATAT TGGGGCATC CGAGTAACG       29

( 2 ) INFORMATION FOR SEQ ID NO: 10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 10:

GTGGCGATAT TGGGCGATC CGAGTAACG       29

( 2 ) INFORMATION FOR SEQ ID NO: 11:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 11:

GCUCGUUGCG GGACUUAACC CAACAU       26

( 2 ) INFORMATION FOR SEQ ID NO: 12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 12:

AUGUUGGGUU AAGUCCCGCA ACGAGC       26

( 2 ) INFORMATION FOR SEQ ID NO: 13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 13:

CTAAAGCGCT TTCCACCACA AGAC       24

( 2 ) INFORMATION FOR SEQ ID NO: 14:

( i ) SEQUENCE CHARACTERISTICS:

(A) LENGTH: 24 base pairs
(B) TYPE: nucleic acid
(C) STRANDEDNESS: single
(D) TOPOLOGY: linear (ii) MOLECULE TYPE: nucleic acid (xi) SEQUENCE DESCRIPTION: SEQ ID NO: 14:

GTCTTGTGGT GGAAAGCGCT TTAG    24

ADDUCT PROTECTION ASSAY

FIELD OF THE INVENTION

The present invention features methods for assaying the presence or amount of an analyte in a sample.

BACKGROUND OF THE INVENTION

Assaying for the presence or amount of an analyte in a sample can provide valuable information such as whether a particular organism, gene, or protein is present in the sample. Analyte assaying can be performed using a binding partner able to recognize and bind a characteristic portion of the analyte. For example, labelled antibodies and oligonucleotide probes can be used in diagnostic assays to detect the presence of an organism, gene, or protein in a sample.

An oligonucleotide probe can hybridize to a complementary target nucleic acid sequence allowing for detection of the target nucleic acid sequence. Detecting the presence or amount of a target nucleic acid sequence can be used in different types of assays including the following: detecting the presence of a microorganism or group of microorganisms in a sample by probing for a nucleic acid sequence characteristic of the microorganism or group of microorganisms (e.g., Hogan et al., entitled "Nucleic Acid Probes for Detection and/or Quantitation of Non-Viral Organisms," International Application No. PCT/US88/03009, International Publication No. WO 88/03957, (hereby incorporated by reference herein); detecting the presence of a virus by probing for a sequence characteristic of the virus (e.g., McDonough et al., entitled "Detection of Human Immunodeficiency Virus Type 1," International Application No. PCT/US94/03130, International Publication No. WO 94/23069, and McDonough et al., entitled "Nucleic Acid Amplification Oligonucleotides and Probes to Human Hepatitis B Virus" International Application No. PCT/US93/04004, International Publication No. WO 93/22469 (both of these references are hereby incorporated by reference herein); and detecting whether a particular nucleic acid sequence is accessible for hybridization to a complementary oligonucleotide (e.g., Nelson et al., entitled "Oligonucleotide Screening Assay" International Application No. PCT/US94/08024, international Publication No. WO 95/03427 (hereby incorporated by reference herein).

Different labels and assay formats can be used to detect the presence or amount of an analyte in a sample. Examples of detectable labels include radioisotopes, fluorescent moieties, chemiluminescent moieties, enzymes, enzyme substrates and ligands.

Overall, assay formats can be characterized as being "heterogenous" or "homogenous" depending upon whether binding partner bound to the analyte is physically separated from binding partner not bound to analyte. Heterogenous assays involve physical separation of binding partner bound to analyte from binding partner not bound to analyte and can be carried out, for example, using supports for binding either binding partner bound to analyte or binding partner not bound to analyte. For example, Arnold et al., International Application No. PCT/US88/00550, Publication No. WO 88/06633 illustrate the use of polycationic supports which can be used in a physical separation step involving polynucleotides and mention other supports which can be used for physical separation of polynucleotides; and Harlow et al., *Antibodies; A Laboratory Manual,* Cold Spring Harbor Laboratory, 1988, describe a sandwich assay where an antibody bound to a support binds the analyte and the analyte is then detected using another antibody, where unbound contaminates are washed from the solid support. (Both of these references are hereby incorporated by reference herein.)

Examples of assays which can be carried out in a homogenous manner include immunoassays described by U.S. Pat. Nos. 3,654,090, 3,817,837, and 4,190,496; assays using chromophores containing fluorescer/quencher pairs described by U.S. Pat. Nos. 4,199,559, 4,174,384, and 4,318,707; assays employing a conjugate formed of a specific binding partner substance coupled to a chemiluminescent reactant where the activity of the chemiluminescent reactant is affected by reaction between the specific binding substance in the conjugate and a specific binding counterpart, as described by Boguslaski et al. U.S. Pat. No. 4,383,031; assays involving polarization fluorescence as described in U.S. Pat. No. 4,668,640; assays using a double probe involving a first probe labelled with a catalyst and a second probe containing an apoluminescer as described by U.S. Pat. No. 4,670,379; assays using an energy transfer system as described by Elazar et al., European Patent Application No. 85105130.0, Publication No. 0 159 719; assays using a chemiluminescent moiety and an absorber/emitter moiety, as described by Heller et al., European Patent Application No. 82303699.1, Publication No. 0 070 685, and Morrison et al., European Patent Application No. 82303700.7, European Publication No. 0 070 686; and assays using a label as described by Arnold et al., U.S. Pat. No. 5,283,174, Nelson et al., "Detection Of Acridinium Esters By Chemiluminescence" in: *Nonisotopic DNA Probe Techniques,* (Kricka ed., Academic Press, 1992) pp. 275–311, Nelson et al., *Clin. Chem. Acta* 194:73–90, 1990, and Arnold et al., *Clin. Chem.* 35:1588–1594, 1989 (each of the references mentioned in this paragraph are hereby incorporated by reference herein).

SUMMARY OF THE INVENTION

The present invention features an adduct protection assay involving the use of a labelled binding partner and a signal altering ligand. The signal altering ligand can preferentially alter the ability of label which is not part of a binding partner:analyte complex to produce a detectable signal, compared to its ability to alter signal produced from label which is part of a binding partner:analyte complex. The presence or amount of analyte can be determined by detecting the signal produced from unaltered label. The adduct protection assay is very versatile. For example, alteration of signal can be carried out under a wide range of conditions (e.g., pH, temperature, and ionic strength), and both label alteration and signal triggering can be carried out at essentially constant temperature to achieve a high degree of sensitivity.

The adduct protection assay is carried out using a binding partner containing a label which can preferably be triggered to produce a detectable signal. A "detectable signal" refers to a change in the environment caused by the label which can be measured. Examples of detectable signals include emission of light and changes in absorbance.

By "triggering" is meant causing a label to produce a detectable signal. In a preferred embodiment signal production is brought about by a triggering agent. Different types of triggering agents can be used to produce a detectable signal from a label. Examples of triggering agent/label pairs include the following: substrate/enzyme or enzyme/substrate causing a change in absorbance; hydrogen peroxide/chemiluminescent label causing light emission; and light/fluorescent label causing light emission.

Preferred labels are those which can be triggered to emit light. The triggering of a light emitting substance brings about the formation of an excited state molecule which emits light.

Adduct formation by a signal altering ligand alters and preferably prevents signal production by the label. A "signal altering ligand" refers to a compound which can associate with a label to form an adduct which alters signal production from the label. Preferably, adduct formation is reversible.

"Alteration of signal production" refers to a change in the type, amount, or kinetics of signal produced from a label. Preferably, the produced signal is light emission and alteration of light emission is achieved by causing one or more of the following: (1) light emission at a different wavelength; (2) a decrease in light emission; and (3) changing the kinetics of light emission. Preferably, adduct formation prevents light emission.

The terms "preferential alteration of signal production" and "discrimination" refer to alteration of signal production from label present on a binding partner not bound to analyte (unbound label) occurring to a greater extent than alteration of signal production from label present on a binding partner bound to analyte (bound label). The difference in signal production by labels present on bound or unbound binding partners is sufficient to enable one skilled in the art to detect the presence and/or amount of analyte. Preferential alteration of signal production can be measured in terms of a differential alteration ratio expressed as the time in which half of the signal produced from label present on a binding partner bound to analyte is altered ($t_{1/2}$ bound label) divided by the time in which half of the label present on a binding partner not bound by analyte is altered ($t_{1/2}$ unbound label).

Thus, a first aspect of the present invention features a method for assaying the presence or amount of an analyte in a sample. The method involves the following steps:

a) exposing the sample to a labelled binding partner;

b) treating the sample with a signal altering ligand able to preferentially alter label present on a binding partner not part of a labelled binding partner:analyte complex; and c) detecting signal produced from label which was not altered.

Detecting signal produced from label which was not altered can be achieved by triggering the label to produce a signal and measuring the production of signal which was not altered. For example, the presence of a light emitting label not altered by a ligand can be achieved by triggering the label to emit light by standard techniques, and measuring the kinetics, amount, or wavelength of light emission.

In a preferred embodiment, labels are light emitting labels such as fluorescent, chemiluminescent and bioluminescent labels. Light emission can be measured using standard equipment such as a luminometer or fluorometer. Preferably, preferential alteration of signal production and light emission is carried out under essentially constant temperature. "Essentially constant temperature" refers to the maintenance of the temperature within a range of no more than 250%, more preferably no more than 100%, more preferably 25%, more preferably 10%, and most preferably 5%. In a more preferred embodiment, preferential label alteration and triggering of light emission are carried out at room temperature (about 20°–25° C.) at essentially constant temperature.

The adduct protection assay can be carried out using different formats. For example, the assay can be performed with or without a separation step. The avoidance of a separation step simplifies the assay and provides advantages such as saving on time, reagents, and simplicity of automation.

A separation step to further remove labelled binding partner not bound to analyte or contaminants can be performed prior to triggering light emission. A separation step is preferred when the assay is used on clinical samples which have not undergone purification.

Thus, the featured assay provides for detecting the presence or amount of an analyte involving preferential alteration of signal produced by a label present on a binding partner not bound to the analyte, thereby allowing signal produced by a label present on a binding partner bound to analyte to be clearly detected. The versatility of the assay has numerous useful aspects including the ability to carry out label alteration under a wide range of buffer conditions to achieve high sensitivity, the ability to carry out the assay using essentially constant temperature to rapidly achieve a high degree of sensitivity, and the ability to carry out the assay at room temperature to achieve a high degree of sensitivity. Advantages of such an assay include ease of use due to less manipulation steps, saving on time, and being more compatible to automation.

Various examples of different aspects and embodiments of the present invention are described herein, such as different label structures and signal altering ligands. Unless stated in the claims, these examples and other examples provided herein are not intended to limit the invention.

Other features and advantages of the invention will be apparent from the following figures, detailed description of the invention, and the claims.

DETAILED DESCRIPTION OF THE INVENTION

Figure 1:
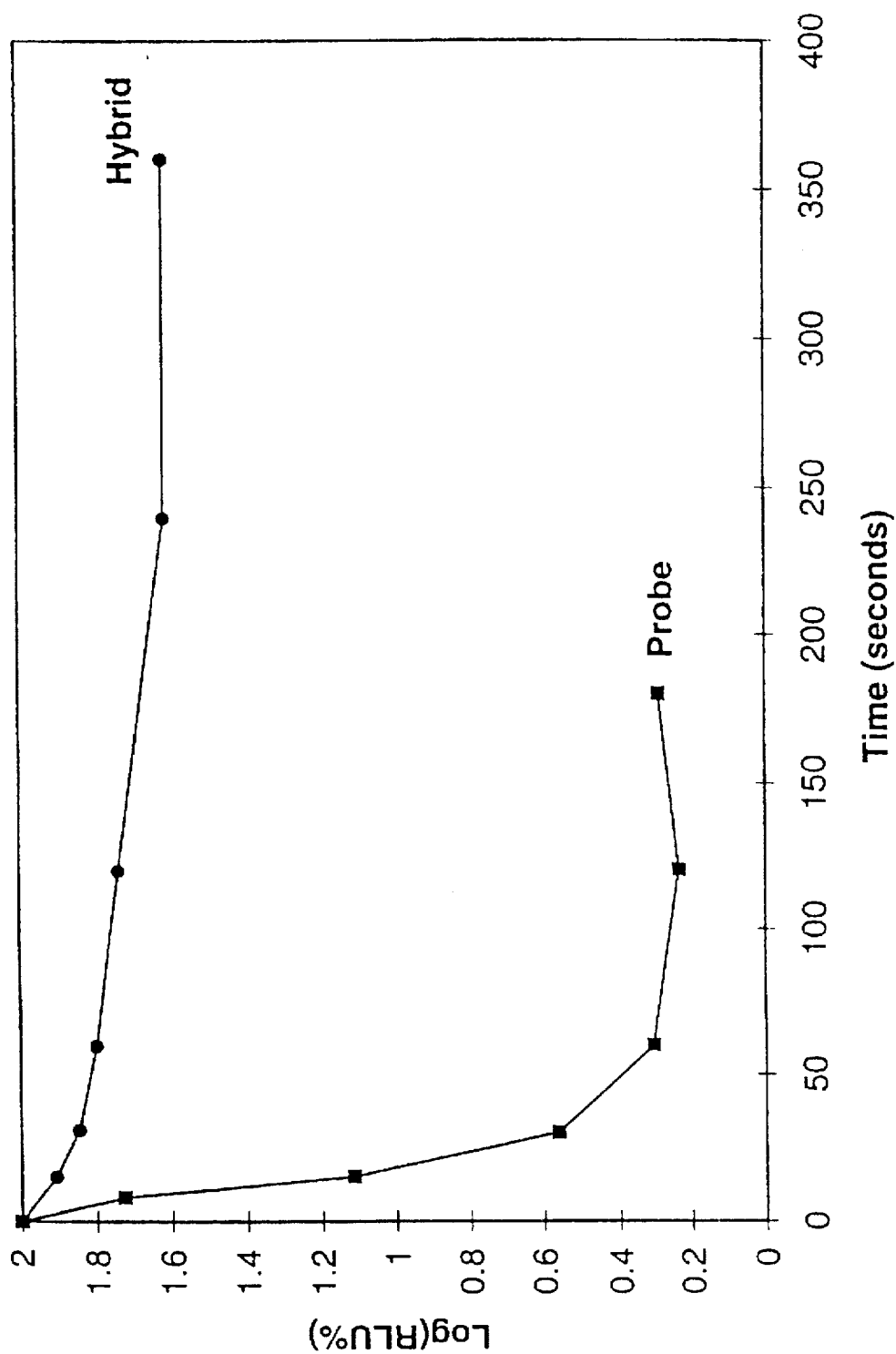
FIG. 1 graphically illustrates preferential alteration of signal production using sodium sulfite and an acridinium ester-labelled probe.

The adduct protection assay facilitates the detection of an analyte by exploiting adduct formation to preferentially alter signal production from a label present on a binding partner not bound to an analyte. The assay involves the formation of a protective micro-environment when a labelled binding partner forms a complex with an analyte. The label present on labelled binding partner bound with analyte is preferentially protected from forming an adduct with a signal altering ligand. The adduct protection assay can be used to rapidly detect the presence and/or amount of analyte with a high degree of sensitivity.

Signal production as an indication of the presence or amount of analyte can be measured at different time points after a preferential signal alteration step is started. In one embodiment, signal production is measured after a time allowing for stable adduct formation, for example at equilibrium. Measuring signal production where adduct formation with label present on bound and unbound binding partners is relatively constant over time may facilitate obtaining reproducible results over a larger time range, and allow for numerous experiments to be performed at one time and the results read at a later time.

In another embodiment, signal is measured at a time after triggering when the ratio of signal produced by label present on bound binding partner to signal produced by label present on unbound partner is maximized. In this regard, the adduct protection assay can proceed more rapidly than hydrolytic assays where label present on unbound binding partner is preferentially altered by cleaving off the leaving group (See, Example 4 and 5 infra). Arnold et al., U.S. Pat. No. 5,284, 174, Nelson et al., "Detection of Acridinium Esters by Chemiluminescence" in: *Nonisotopic DNA Probe Techniques*, (Kricka ed., Academic Press, 1992) pp. 275-311, Nelson et al., *Clin. Chem. Acta* 194:73-90, 1990 and Arnold et al., *Clin. Chem.* 35:1588-1594, 1989, describe assays which can preferably be carried out by preferential hydrolytic cleavage of label present on unbound binding partner. (Each of these references are hereby incorporated by reference herein.)

Adduct formation occurring with label present on bound or unbound binding partners is illustrated by Equations 1 and 2, where "Unbound Label" refers to label present on binding partner not complexed with analyte, "Bound Label" refers to label present on binding partner complexed with analyte, "Ligand" refers to a signal altering ligand, "Label*" indicates the label can be triggered to produce a signal, and "Label-Ligand" indicates the formation of a signal altering adduct.

Unbound Label* + Ligand = Unbound Label – Ligand      Equation 1

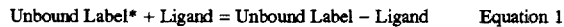

Bound Label* + Ligand = Bound Label – Ligand      Equation 2

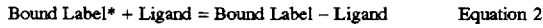

Preferential alteration of signal production is affected by the differences in $K_1$ and $K_2$, and the rate in which the two reactions reach equilibrium. A higher Equation 1 equilibrium constant results in more label present on unbound binding partner being altered at equilibrium. A lower Equation 2 equilibrium constant results in less label present on bound binding partner being altered at equilibrium. As the reaction represented by Equation 1 proceeds at a faster rate than Equation 2, more label present on unbound binding partner is preferentially altered during the initial reactions with signal altering ligands.

Factors affecting preferential alteration of signal production include the amount and type of analyte, the amount and type of labelled binding partner, the amount and type of ligand, and possible interactions with other components present during the assay. Thus, the design and components of a particular assay should take into account the nature and source of the analyte, the type of signal altering ligand used, the nature of the labelled binding partner, the ability of the binding partner to complex with the analyte to form a protective micro-environment for the label, and the environment in which the assay is taking place.

I. Sensitivity

The present invention can be used to detect the presence of an analyte with a high degree of sensitivity. Sensitivity reflects the ability of an assay to accurately detect the presence of an analyte. Sensitivity takes into account the background resulting from both signal production from label present in unbound binding partner which was not altered and the ability of the signal altering ligand to discriminate between label present on bound and unbound binding partners.

FIG. 1 illustrates the relationship between preferential alteration of signal production and background. Each curve illustrates triggering of light emission in the presence of a signal altering ligand. The hybrid curve refers to bound label protected from signal alteration, while the probe curve refers to label present on unbound binding partner. The $t_{1/2}$ values for calculating the differential alteration ratio can be obtained from the slopes of the two curves. The points were the two curves level off indicate that equilibrium was reached. The point where the probe curve levels off also indicates background noise.

For oligonucleotide probes used to detect a nucleic acid analyte, the differential alteration ratio is determined by measuring the $t_{1/2}$ of the hybrid divided by the $t_{1/2}$ of the labelled probe. Preferably, the differential alteration ratio is at least 2-fold, more preferably at least 15-fold, even more preferably at least 75-fold, and most preferably at least 100-fold.

More preferably, the assay is carried out under conditions of high sensitivity where the signal produced is equal to, or greater, than the mean of the background plus two times the standard deviation. Standard deviation can be calculated using standard techniques and equations as follows:

$$S.D. = \sqrt{\frac{\sum_{i=1}^{n} (x_i - \bar{x})^2}{n-1}} \qquad \text{Equation 3}$$

Where $\bar{x}$ is the sample mean, $x_i$ is a particular reading, and n is the total number of measurements.

More preferably, the assay is carried out under conditions where the signal produced is equal to, or greater, than the mean of the background plus three times the standard deviation, more preferably at least 4 times the standard deviation, and most preferably at least 5 times the standard deviation.

II. Analyte

The adduct protection assay can be used to detect the presence and/or amount of different types of analytes, including nucleic acid sequences and antigenic epitopes. The amount of analyte present in a sample depends on the sample being assayed and whether any techniques are carried out to increase the amount of analyte prior to detection. For example, the number of nucleic acid analytes can be increased using techniques such as PCR (e.g., as described by Mullis et al., U.S. Pat. No. 4,683,202), and transcription-based amplification (e.g., as described by Kacian et al., in U.S. Pat. No. 5,399,491) (both these references are hereby incorporated by reference herein).

A. Detection of Target Nucleic Acids

Detection of a target nucleic acid sequence (e.g., a nucleic acid sequence sought to be detected or measured), can be carried out using a nucleic acid probe which is sufficiently complementary to the target nucleic acid sequence to distinguish the sequence from other nucleic acid sequences which may be present in the sample. Probe specificity is affected by numerous factors known in the art such as the degree of complementarity between the probe and target nucleic acid sequences and the hybridization conditions. (E.g., see Sambrook et al., *Molecular Cloning: A Laboratory Manual* (Cold Spring Harbor Laboratory Press, 1989) (hereby incorporated by reference herein into the present application) and Hogan et al., PCT/US88/03009, supra.)

B. Antigen Detection

Antibodies can be used to detect the presence of a particular epitope present on an antigen. Harlow et al., *Antibodies; A Laboratory Manual*, Cold Spring Harbor Laboratory, 1988 (hereby incorporated by reference herein), describes production and use of antibodies.

III. Labelled Binding Partner

Labelled binding partners comprise a label joined with a binding partner. The binding region enables the binding partner to bind to an analyte, while the label can be triggered to produce a detectable signal.

The adduct protection assay can be carried out with an excess amount of labelled binding partner or an excess amount of analyte. Providing an excess amount of labelled binding partner offers the advantage of increased sensitivity at low analyte concentrations. A possible disadvantage to having excess label is that more labelled binding partner is present, thereby requiring more ligand to reduce background. Nevertheless, because of the high sensitivity which can be achieved with the adduct protection assay, an excess amount of labelled binding partner is preferred for carrying out the assay.

A. Labels

The adduct protection assay can be carried out using different types of labels such as colorimeteric, bioluminescent, fluorescent and chemiluminescent labels. Factors to be considered in label selection include the following: (1) the label should be chosen so its ability to be triggered to produce a signal can be altered by adduct formation, (2) the label can be protected from adduct formation by the protective micro-environment formed upon binding of the binding partner to the analyte, and (3) the label does not prevent the binding partner from recognizing the analyte.

Examples of colorimeteric labels include labels containing an enzyme which can combine with a substrate to produce a product causing a change in absorbance and labels containing a substrate which can combine with an enzyme to produce a change in absorbance. For example, the signal altering ligand can alter the signal from the enzyme/substrate by forming an adduct with the enzyme/substrate thereby altering the enzyme catalyzed reaction. Another example, are labels that absorb light at a given wavelength and this absorbance is altered by reaction with a ligand.

The present invention is preferably performed using nucleic acid probes having a light emitting label which is protected from adduct formation by hybridization of probe to a target nucleic acid. Preferred light emitting labels are chemiluminescent or fluorescent. Chemiluminescent labels can be triggered by a chemical reaction such as heating and oxidation, while fluorescent labels can be triggered by light. Labels which can be caused to emit light are generally able to fluoresce, though in some cases triggering of a "chemiluminescent" label by light may result in lesser light emission than chemiluminescence.

1. Chemiluminescent Labels

Chemiluminescent labels are triggered to emit light by a triggering agent which causes the formation of an excited state molecule which decays, thereby emitting light. The chemiluminescent label may contain a leaving group joined to a chemiluminescent molecule which is cleaved during the chemical reaction causing light emission. Alternatively, the chemiluminescent label may not contain a leaving group cleaved during triggering of light emission. Examples of chemiluminescent molecules having a leaving group which may be cleaved during triggering of light emission are described below. Examples of chemiluminescent molecules not having a leaving group cleaved during triggering include dioxetans, oxalates, dioxetanones, and rhuthenium chelates. Examples of different types of chemiluminescent molecules are provided by Campbell, *Chemiluminescence: Principles and Application in Biology and Medicine*, Ellis Horwood Ltd. Chichester England, 1988 (hereby incorporated by reference herein).

Figure 2:
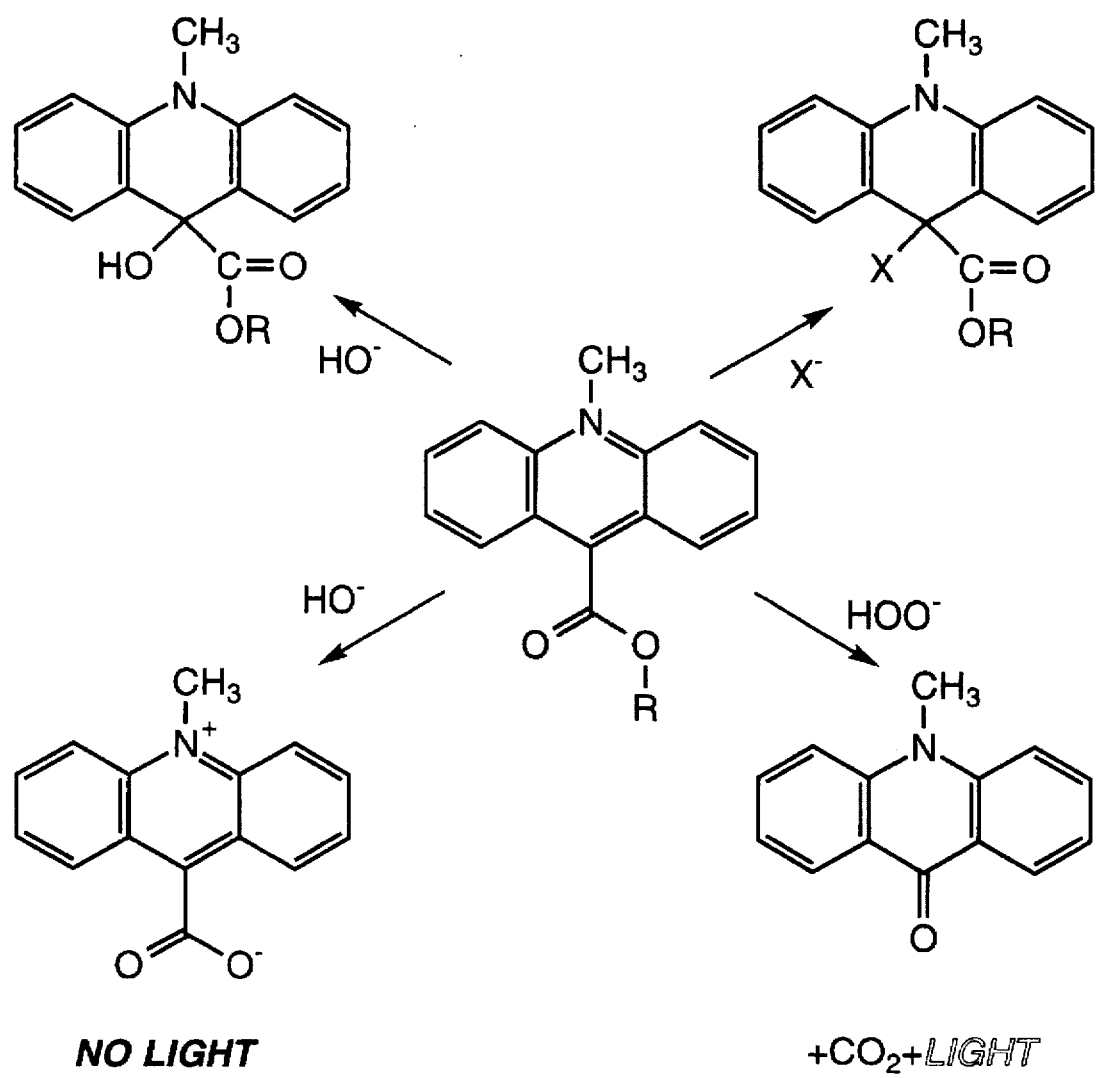
FIG. 2 illustrates the triggering of light emission of a chemiluminescent molecule using hydrogen peroxide.

FIG. 2 illustrates the light emitting reaction of a chemiluminescent label using hydrogen peroxide as a triggering agent. Favorable conditions for triggering a chemiluminescent label and methods of detecting emitted light are known in the art. E.g., see Nelson et al., "Detection Of Acridinium Esters By Chemiluminescence" supra., and Arnold et al., U.S. Pat. No. 5,283,174, supra.

Examples of chemiluminescent labels, the production of such labels, the joining of the labels to binding partners, and factors generally affecting stability of chemiluminescent labels are known in the art. See, Beheshti et al., U.S. Pat. No. 5,290,936; Campbell et al., U.S. Pat. No. 4,946,958; Law et al., U.S. Pat. Nos. 4,918,192, 4,745,181, 5,110,932 and 5,241,070; Mattingly et al.t entitled "Chemiluminescent Acridinium and Phenantridinium Salts," European Patent Application No. 87114490.3, Publication No. 0 273 115; McCapra et al., U.S. Pat. No. 5,281,712; McCapra, U.S. Pat. No. 5,283,334; McCapra et al., U.S. Pat. No. 5,284,951; McCapra, U.S. Pat. No. 5,321,136; McCapra et al., entitled "Assays Utilizing Improved Chemiluminescent Esters, Thioesters and Amides," European Patent Application No. 88121915.8, European Patent Publication No. 0 322 926; Ramakrishnan et al., U.S. Pat. No. 5,284,952; Reddy et al., entitled "Chemiluminescent Compounds" International Application No. PCT/US91/06861, International Publication No. WO 92/09580; Sato et al., entitled "Acridinium Compounds and Conjugates Thereof," European Patent Application No. 94101664.4, European Publication No. 0 609 885; and Sheehan et al., U.S. Pat. No. 3,539,574 (each of these references are hereby incorporated by reference herein). These factors include the structure of the chemiluminescent molecule, the type and position of substituents on the chemiluminescent molecule and on the leaving group, and the structure of the linking group joining a leaving group to a chemiluminescent molecule. For example, different types of linking groups may be present including esters, amides, thiolesters, and sulfonylamides; the stability of the chemiluminescent molecule may be affected by the placement of bulky groups and electron withdrawing or donating groups at certain positions; and preferred leaving groups for efficient chemiluminescence have a $pK_a \leq 11$, preferably $<11$, more preferably 5 to 8, and are more preferably an aryl ring or ring system.

Aizawa et al., entitled "Method of Making Acridinium Derivatives Luminesce and Method of Detecting Test Material Therewith," European Patent Application No. 93919625.1, Publication No. 0 617 107 A1, describe the production and use of superoxide anion ($O^{2-}$) for triggering light emission of acridinium derivatives (this reference is hereby incorporated by reference herein). The methods described by Aizawa et al., are indicated to be suitable for generating light emission at neutral pH.

Preferred chemiluminescent labels contain a chemiluminescent molecule with an aryl ring system and a leaving group. Preferably, the aryl ring system has 1 to 4 aryl groups and contains a positive charge (e.g., the positive charge is present either by being localized on a ring or being localized on a ring substituent). More preferably, the positively charged aryl ring system contains a substituted heterocyclic aryl.

Preferred chemiluminescent molecules having a leaving group have the following structure:

Structure I

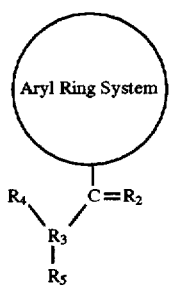

where the aryl ring system comprises one to four cyclic groups, and one of the groups is joined to linking carbon "c," more preferably the aryl ring system is positively charged, more preferably the aryl ring system contains a positively charged heterocyclic aryl joined to "c"; examples of heterocyclic aryls include acridinium, benz[a]acridinium, benz[b]acridinium, benz[c]acridinium, a benzimidazole cation, quinolinium, isoquinolinium, quinolizinium, cyclic substituted quinolinium, pyridinium, pyrimidininium, pyridazinium, pyrazininium, phenathridinium and quinozalinium;

$R_2$ is selected from the group consisting of S, O, and NH, preferably $R_2$ is O;

$R_3$ is selected from the group consisting of O, N, S, halogen, substituted phosphorous, substituted sulfur, substituted boron, and substituted arsenic, preferably $R_3$ is either O, N, or S, more preferably $R_3$ is O or S, most preferably $R_3$ is O;

$R_4$ is selected from the group consisting of alkyl, alkenyl, aryl, alkoxy, and aryloxy, or is absent when $R_3$ is halogen, preferably $R_4$ is an aryl, more preferably $R_4$ is an optionally substituted phenyl; and $R_5$ is nothing unless $R_3$ is N, if $R_3$ is N then $R_5$ is selected from the group consisting of hydrogen, alkyl, alkenyl, aryl, alkoxy, and aryloxy, preferably $R_5$ is nothing.

Positively charged Structure I compounds are ionically associated with a counter-ion. Various different anions such as a halogen, sulfate, alkylsulfate, halosulfate, haloborate, haloacetate, halophosphate, and phosphate can serve as a counter-ion.

More preferably, the chemiluminescent label is made up of an acridinium joined to it leaving group as illustrated in Structure II.

Structure II

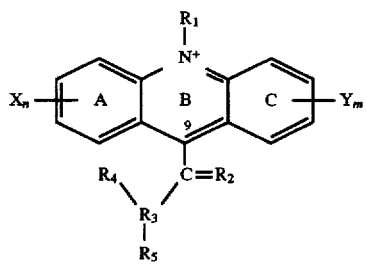

where $R_1$ is selected from the group consisting of H, alkyl, alkenyl, alkynyl, and aryl; preferably $R_1$ is a lower alkyl, more preferably methyl;

n is either 0, 1, 2, 3, or 4, preferably n is either 0, 1 or 2;

m is either 0, 1, 2, 3, or 4; preferably m is either 0, 1, or 2;

each X is independently selected from the group consisting of alkyl, alkenyl, alkynyl, aryl, amino, substituted amino, carboxy, hydroxy, alkoxy, nitro, sulfonyl, halogen, thiol, amido, acetyl, substituted acetyl, and aryloxy, and the remaining A ring substituents are hydrogen, preferably each X is independently an alkyl or an alkoxy, more preferably each X is independently a lower alkyl or a lower alkoxy, most preferably each X is independently methyl or methoxy;

each Y is independently selected from the group consisting of alkyl, alkenyl, alkynyl, aryl, amino, substituted amino, carboxy, hydroxy, alkoxy, nitro, sulfonyl, halogen, thiol and aryloxy, and the remaining C ring substituents are hydrogen, preferably each Y is independently an alkyl or an alkoxy, more preferably each Y is a lower alkyl or a lower alkoxy, and most preferably each Y is independently methyl or methoxy; and $R_2$, $R_3$, $R_4$ and $R_5$ are defined as described above for a Structure I compounds.

Other more preferred chemiluminescent molecules joined to leaving groups have a heterocyclic ring system selected from the group consisting of: benz[a]acridinium, benz[b] acridinium, benz[c]acridinium, benzimidazole cation, quinolinium, isoquinolinium, quinolizinium, cyclic substituted quinolinium, pyridinium, pyrimidininium, pyridazinium, pyrazininium, phenathridinium and quinozalinium; where each ring of the ring system is substituted in the same manner as a Structure II compound where each available carbon can each independently have a X/Y substituent, more preferably each ring contains 0 to 2 substituents; and one of the rings is a positively charged heterocyclic ring containing a N joined to $R_1$ and a carbon atom joined to a linking group.

2. Fluorescent Labels

Fluorescent labels typically contain an aromatic group which can be excited by light to produce an excited state molecule. Binding of the signal altering ligand can alter fluorescence. As noted above, chemiluminescent labels such as acridinium esters can also be fluorescent labels. Thus, examples of fluorescent labels include those labels described as chemiluminescent in Section III.A.1 supra. Examples of fluorescent labels also include intercalators or groove binders such as rhodamine, fluorescein, ruthenium, ethidium halides, and acridine.

Preferred fluorescent labels have a conjugated pi electron system, preferably an aromatic ring. Fluorescence from the aromatic ring can be altered by disrupting the aromaticity of the aromatic ring as, for example, by adduct formation.

3. Chemical Definitions

The following is a description of some of the chemical groups which may be present in the different labels. The different basic chemical structures provided herein can be substituted by different groups. Substitutions of each of the different groups described below can be made with atom or atoms which are non-reactive (i.e., does not react with the analyte, prevent signal altering adduct formation, or prevent signal production). Examples of substitutions to a basic structure are also provided below.

An "acetyl" refers to C(=O)—CH$_3$.
An "amino" refers to —NH$_2$.
An "amido" refers to C(=O)—NH$_2$.

An "alkyl" group refers to an optionally substituted saturated aliphatic hydrocarbon, including straight-chain, branched-chain, and cyclic alkyl groups. Preferably, the alkyl group has 1 to 25 carbons and contains no more than 20 heteroatoms. More preferably, it is a lower alkyl of from 1 to 12 carbons, more preferably 1 to 4 carbons. Heteroatoms are preferably selected from the group consisting of nitrogen, sulfur, phosphorus, and oxygen.

An "alkenyl" group refers to an optionally substituted hydrocarbon containing at least one double bond, including straight-chain, branched-chain, and cyclic alkenyl groups, all of which may be optionally substituted. Preferably, the alkenyl group has 2 to 25 carbons and contains no more than 20 heteroatoms. More preferably, it is a lower alkenyl of from 2 to 12 carbons, more preferably 2 to 4 carbons. Heteroatoms are preferably selected from the group consisting of nitrogen, sulfur, phosphorus, and oxygen.

An "alkynyl" group refers to an optionally substituted unsaturated hydrocarbon containing at least one triple bond, including straight-chain, branched-chain, and cyclic alkynyl groups, all of which may be optionally substituted. Preferably, the alkynyl group has 2 to 25 carbons and contains no more than 20 heteroatoms. More preferably, it is a lower alkynyl of from 2 to 12 carbons, more preferably 2 to 4 carbons. Heteroatoms are preferably selected from the group consisting of nitrogen, sulfur, phosphorus, and oxygen.

An "aryl" refers to an optionally substituted aromatic group having at least one ring with a conjugated pi electron system and includes carbocyclic aryl, heterocyclic aryl, biaryl, and triaryl groups. Examples of aryl substitution substituents include alkyl, alkenyl, alkynyl, aryl, amino, substituted amino, carboxy, hydroxy, alkoxy, nitro, sulfonyl, halogen, thiol and aryloxy.

A "carbocyclic aryl" refers to an aryl where all the atoms on the aromatic ring are carbon atoms. The carbon atoms are optionally substituted as described above for an aryl. Preferably, the carbocyclic aryl is an optionally substituted phenyl.

A "heterocyclic aryl" refers to an aryl having 1 to 3 heteroatoms as ring atoms in the aromatic ring and the remainder of the ring atoms are carbon atoms. Suitable heteroatoms include oxygen, sulfur, and nitrogen. Examples of heterocyclic aryls include furanyl, thienyl, pyridyl, pyrrolyl, N-lower alkyl pyrrolo, pyrimidyl, pyrazinyl, and imidazolyl. The heterocyclic aryl is optionally substituted as described above for an aryl.

An "alkoxy" refers to "-O-alkyl" where "alkyl" is defined as described above and "O" is an oxygen. Preferably, the alkoxy is a O-lower alkyl.

An "aryloxy" refers to a "-O-aryl" where the "aryl" is defined as described above and "O" is an oxygen.

"Nitro" refers to $NO_2$.

"Sulfonyl" refers to $S(O)_2$—R, where R a non-reactive atom or atoms. Examples of R include alkenyl, alkynyl, aryl, halogen, amino, and substituted amino.

A "substituted acetyl" refers to $C(=O)$—$CH(R)_2$, where each R is any non-reactive chemical atom or atoms, provided that at least one R is not hydrogen. Examples of such substitutions include hydrogen, alkyl, alkenyl, alkynyl, aryl, amino, carboxy, and alkoxy.

A "substituted amino" refers to —NH—R where R is any non-reactive chemical atom or atoms. Examples of such substitutions include alkyl, alkenyl, alkynyl, aryl, amino, carboxy, and alkoxy.

A "substituted phosphorous" refers to —$P(R)_3$ where each R is any non-reactive chemical atom or atoms. Examples of R include O, =O, S, $CH_3$, Se, and As.

A "substituted sulfur" refers to the presence of any atom or atoms other than hydrogen which obey chemical stoichiometry and is non-reactive.

A "substituted boron" refers to the presence of any atom or atoms other than hydrogen which obey chemical stoichiometry and is non-reactive.

A "substituted arsenic" refers to the presence of any atom or atoms other than hydrogen which obey chemical stoichiometry and is non-reactive.

B. Binding Region

A binding region is designed to recognize part of the analyte and allow for the formation of a micro-environment with an analyte which protects the label from signal alteration by adduct formation. Preferably, the binding region contains a nucleic acid sequence complementary, to some degree, to a target nucleic acid sequence. For example, an oligonucleotide probe can be designed to specifically hybridize to a target nucleic acid sequence characteristic of a particular microorganism. On the other hand; a hybridization probe without a high degree of specificity can be used in different assays. Examples of applications in which a high degree of specificity of the probe is not required include those where the probe is designed to hybridize to more than one related sequence, and where the target nucleic acid is separated from contaminants. Target nucleic acid can be separated from contaminants, for example, by using a capture probe (e.g., see Collins entitled "Target and Background Capture Methods and Apparatus for Affinity Assays" European Patent Application No. 87309308.2, European Publication No. 0 265 244 B1, hereby incorporated by reference herein).

Another example of a binding region is an antibody epitope binding domain. Antibodies can be used to detect the presence of a particular epitope present on an antigen. For example, antibodies can be used to detect particular antigenic protein. Harlow et al., *Antibodies; A Laboratory Manual*, Cold Spring Harbor Laboratory, 1988 (hereby incorporated by reference herein), describes production and use of antibodies.

C. Labelled Binding Partner Synthesis

Binding partners containing labels can be produced using standard techniques. Overall, the label should have a structure allowing it to be present in the protective micro-environment formed by binding of the binding partner to the analyte, while at the same time allowing a triggering agent to cause signal production. For example, when light emission of chemiluminescent molecules is triggered by oxidic attack, the linking group should remain susceptible to oxidic attack when present in the micro-environment.

The label should not prevent the binding partner from binding to the analyte and distinguishing the analyte from contaminants. For example, the ability of a labelled nucleic acid probe to indicate the presence of a particular organism should remain intact.

Nucleic acid probes having a particular nucleic acid sequence and base composition can be constructed using standard techniques. Modification of the base composition can be carried out, for example, to increase the stability of the oligonucleotide by alkylation of the 2'-O-position (e.g., a 2'-methoxy group) (see., Miller et al., entitled "Oligonucleotides Modified to Improve Stability at Acid pH," International Application No. PCT/US94/00157, International Publication No. WO 94/15619 (hereby incorporated by reference herein). Organic synthesis of oligonucleotides can be carried out by adding nucleotides in a step wise fashion. Eckstein, F., *Oligonucleotides and Analogues, A Practical Approach*, chapters 1–5, 1991, reviews organic synthesis of oligonucleotides; Caruthers, et al., In *Methods In Enzymology* vol. 154 p. 287 (1987), describe a procedure for organic synthesis of oligonucleotides containing phosphodiester linkages using standard phosphoramidite solid-phase chemistry; Bhatt, U.S. Pat. No. 5,252,723 describes a procedure for organic synthesis of oligonucleotides containing phosphorothioate linkages; and Klem et al., entitled "Improved Process for the Synthesis of Oligomers" PCT WO 92/07864, describe organic synthesis of oligonucleotides having different internucleotide linkages including methylphosphonate linkages. (Each of these references are hereby incorporated by reference herein.)

A label can be joined to a nucleic acid binding partner using techniques such as those described by Arnold et al., entitled "Non-Nucleotide Linking Reagents for Nucleotide Probes" EPO Application Number 88308766, Publication No. EP 313219; Arnold et al., U.S. Pat. No. 5,185,439; and Nelson et al., "Detection of Acridinium Esters by Chemiluminescence" in: *Nonisotopic DNA Probe Techniques*, (Kricka ed., Academic Press, 1992) pp. 275–311. These references focus on producing a binding partner containing an acridinium ester joined to a nucleic acid binding region. However, analogous techniques can be used to join other labels to other binding partners. (Additional references for producing binding partners joined to labels are mentioned in Section III.A.1 supra.)

Light emitting molecules can be joined to antibodies using techniques such as those described by Weeks et al., Immunoassays using acridinium esters, *Methods Enzymol* 133:366–368 1986), and references mentioned in Section III.A.1 supra, concerned with joining light emitting labels to antibodies. Antibodies can be produced using standard techniques such as those described by Harlow et al., supra.

IV. Signal Altering Ligand

Signal altering ligands suitable for the adduct protection assay can discriminate between label present on an unbound binding partner and label present on binding partner bound to analyte. The amount of ligand used in an assay can effect the assay in different ways. For example, providing more ligand can increase the number of altered labels present on bound and unbound binding partners.

Preferred ligands are those which quickly react with label present on unbound binding partner and/or which provide a high Equation 1 equilibrium constant, while reacting very slowly with label present on binding partner bound to analyte and/or having a low Equation 2 equilibrium constant. More preferably, the signal altering ligand quickly reacts with label present on binding partner not bound to analyte providing a high Equation 1 equilibrium constant, and reacts slowly with label on bound binding partner providing a low Equation 2 equilibrium constant.

Preferred signal altering ligands are nucleophiles able to discriminate between label present on bound and unbound binding partners under assay conditions and which form a strong adduct with label present on unbound binding partner. For example, in the case of preferred light emitting labels having a linking group joined to a leaving group, the formed adduct should inhibit the linking group from being oxidized by oxidic agents such as hydrogen peroxide and superoxide ion. Arnold et al., U.S. Pat. No. 4,950,613 and Hammond et al., *J. Biolumin. Chemilumin.* 6:35–43, 1991, describe ligands able to form a protective adduct with an acridinium ester preventing light emission. (Both these references are hereby incorporated by reference herein.)

Preferred ligands have a lone pair of electrons enabling the ligand to act as a strong nucleophile. More preferably, the lone pair of electrons are present on a group VI element, most preferably the element is sulfur. Preferably, the element containing the lone pair of electrons is not adjacent to a conjugated pi electron system or a nitrile group. For example, the element containing the lone pair of electrons should not be adjacent to an aromatic ring. Examples of suitable signal altering ligands include tetrahydrothiopene, propanethiol, benzylmercaptan, sulfite, glycol sulfite, hydrosulfite, metabisulfite, thiosulfate, thiophosphate, metaarsenite, tellurite, arsenite, and thiocyanate.

V. Detection of Nucleic Acid Target Sequences

The adduct protection assay is preferably performed using a nucleic acid probe to detect the presence of a target nucleic acid sequence. The degree of protection afforded by a labelled-probe:target hybrid to a label is influenced by factors including the type of nucleotide bases present and the nucleotide sequences of the probe and hybrid.

The adduct protection assay can be used to detect different nucleic acid targets such as DNA and RNA. The assay is preferably carried out using RNA targets. Methods for producing RNA and amplifying RNA targets starting with DNA, or amplifying RNA targets starting with RNA, are known in the art. E.g. Kacian et al., U.S. Pat. No. 5,399,491.

VI. Examples

Examples are provided below to illustrate different aspects and embodiments of the present invention. These examples illustrate the present invention using acridinium esters as a label. Acridinium esters, like many other cationic heteroaromatic species, react reversibly with nucleophiles to form adducts. As a result of adduct formation, several important properties of acridinium ester are markedly altered. The preferred site for adduct formation on acridinium ester is the C-9 position. Adduct formation alters the visible spectrum of acridinium ester, strongly inhibits acridinium ester fluorescence, stabilizes the ester bond of acridinium ester to hydrolysis, and inhibits the reaction of a triggering agent such as peroxide ion or superoxide ion with acridinium ester to generate chemiluminescence.

These examples are not intended in any way to limit the disclosed invention. The examples illustrate methodology by which different labels and signal altering ligands can be readily identified by routine procedures to ensure that they have the desired activity. For example, labels within a formula described herein can be screened to determine those labels with the most appropriate activity.

EXAMPLE 1

Preferential Discrimination of Label on Bound and Unbound Binding Partners

Compounds containing sulfur atoms having a free electron pair which are not conjugated to an aromatic ring or a nitrile group were found to form strong adducts with acridinium ester-labelled single-stranded probes, but not with the same probes hybridized to a target nucleic acid analyte. This example illustrates the use of a signal altering ligand to preferentially alter label present on unbound binding partner.

Hybridization

To 15 µl of 2× hybridization buffer (100 mM lithium succinate (pH 5.2), 8.5% (w/v) lithium lauryl sulfate, 1.5 mM EDTA, 1.5 mM EGTA) was added 1 pmol of acridinium ester (AE)-labelled probe ($7 \times 10^7$ RLU/pmol) and 4 pmol of target. The AE-labelled probe sequence is provide by SEQ. ID. NO. 1: 5'-GGGGTTCTT*T TCGCCTTTCC CTCACGG, where * indicates the position of the acridinium ester label. The target sequence is provided by SEQ. ID. NO. 2: 5'-CCGTGAGGGA AAGGCGAAAA GAACCCC.

The resultant solution was adjusted to 30 µl with water, heated at 60° C. for 30 minutes and diluted to 500 µl with 1× hybridization buffer.

Adduct Protection

In a 12×75 mm tube (Sarstedt) was added 2 µl of AE-labelled probe or hybrid (400,000 RLU). To this solution was added 100 µl of adduct forming buffer (10 mM sodium sulfite, 30 mM borate buffer (pH 8.7), 1.5% Triton TX100). The solution was then vortexed and allowed to sit at room temperature (about 22°–25° C.) for different amounts of time. Chemiluminescence of the resultant solution was measured by injection of Detect I (0.1% (v/v) $H_2O_2$ in 0.001N $NHNO_3$) followed 0.5–2 seconds later by injection of Detect II (200 µl of 1N NaOH). Light emission was integrated over a 5-second interval.

Results

As shown in FIG. 1, sodium sulfite reacts very rapidly with AE-probe and after 150 seconds the reaction reaches equilibrium. In contrast, when the same AE-probe is hybridized to a complementary nucleic acid target the resultant AE-hybrid reacts much more slowly with sodium sulfite.

At lower concentrations of sodium sulfite, less adduct forms with acridinium ester but adduct formation is still stronger and faster on AE-probe versus AE-hybrid. At higher concentrations of sodium sulfite (200 mM) more adduct forms on acridinium ester but discrimination between AE-probe and AE-hybrid is decreased.

EXAMPLE 2

Detection of a Target Sequence

The ability of the adduct protection assay to detect the presence of a target sequence was examined using a large excess of acridinium ester-labelled probe and decreasing amounts of a complementary target.

Hybridization

To 20 µl of hybridization buffer was added various amounts of target and 0.05 pmol of probe. The AE-labelled probe sequence is provide by SEQ. ID. NO. 3: 5'-ATCATCCATG TATTGAT*AGA TAACTATGTC TGG, where * indicates the position of the acridinium ester label. The target sequence is provided by SEQ. ID. NO. 4: 5'-CCAGACATAG TTATCTATCA ATACATGGAT GAT. The resultant solution was then heated to 60° C. for 30 minutes.

Adduction Protection

To a 12×75 mm tube (Sarstedt) was added 200 µl of adduct forming solution (60 mM sodium tetraborate (pH 8.8), 2% (v/v) TX100, 20 mM sodium sulfite). The solution was vortexed and incubated 15 seconds at room temperature. Chemiluminescence of the resultant solution was measured by injection of Detect I followed 0.5 seconds later by injection of Detect II. Light emission was integrated over a 5-second period of time.

Results

Figure 3:
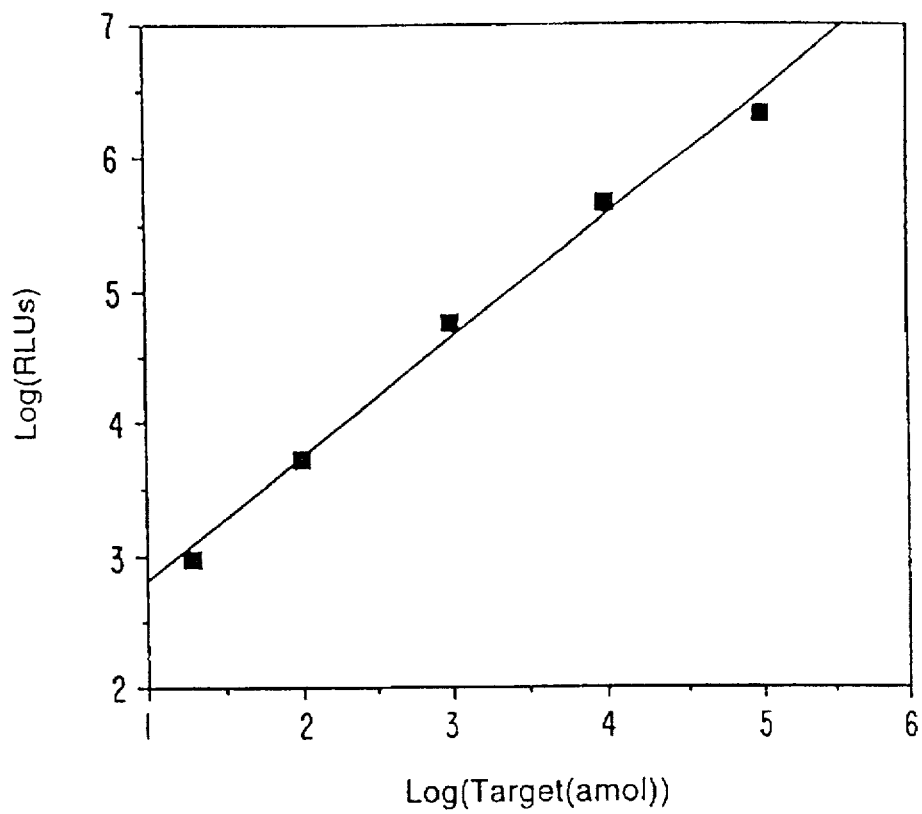
FIG. 3 illustrates the adduct protection assay using increasing amounts of target.

As shown in FIG. 3 the adduct protection assay was able to detect the presence of a target sequence using a large excess of acridinium ester-labelled probe and decreasing amounts of a complementary target.

EXAMPLE 3

Different Acridinium Ester Structures

Figure 5:
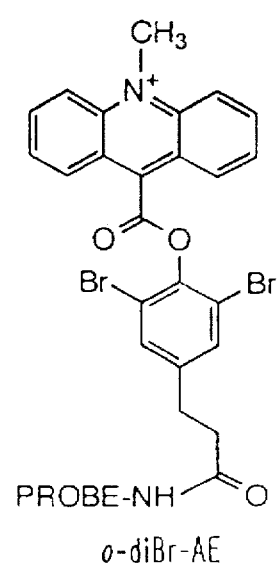
FIGS. 4 and 5 provide examples of binding partners containing an acridinium ester label joined to a binding region. The binding region is indicated in the figures by "probe."
Figure 4:
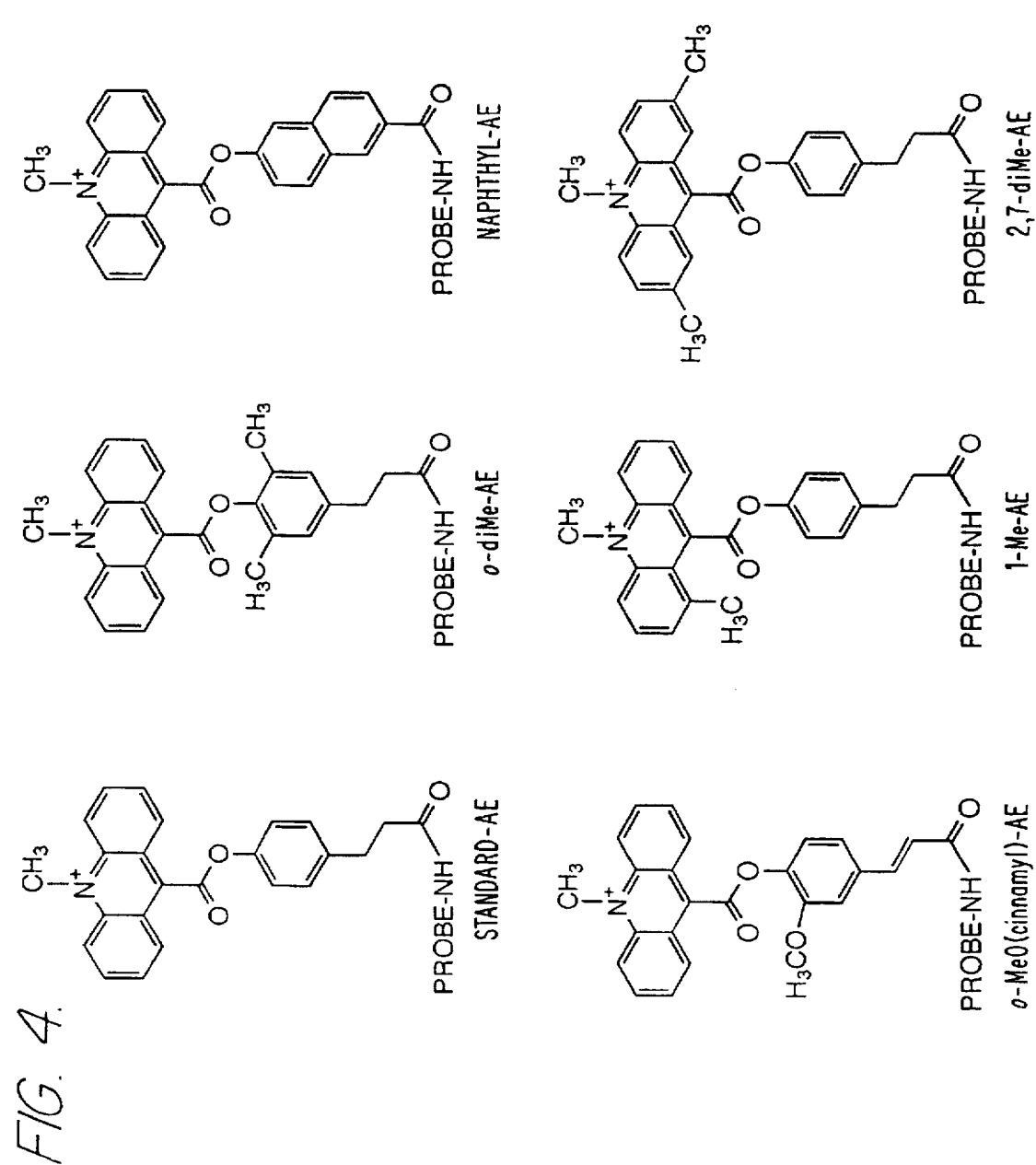

This example illustrates the use of different acridinium ester derivatives in the adduct protection assay and the effect different acridinium ester derivative structures have on adduct formation rates. The effect of electron donating groups on the acridinium ring were examined using 1-methyl-AE and 2,7 dimethyl-AE. The effect of different leaving groups linked to nucleic acid were examined using o-AE, naphthyl AE, o-Me-Cin-AE, o-diMe-AE, and o-diBr-AE. The structure of these different acridinium esters are shown in FIGS. 4 and 5. Sodium sulfite or sodium metabisulfite were used as the signal altering ligand.

Hybridization

To 15 µl of 2× hybridization buffer (0.2M lithium succinate (pH 5.2), 1.0M LiCl, 0.2% Triton X-100) was added 0.1 pmol of probe ($7×10^7$ RLU/pmol) and 0.1 pmol of DNA target. The AE-labelled probe sequence is provided by SEQ. ID. NO. 5: 5'-GCTCGTTGCG GGACTT*AACC CAACAT, where * indicates the position of the acridinium ester label. The target sequence is provided by SEQ. ID. NO. 6: 5'-ATGTTGGGTT AAGTCCCGCA ACGAGC. The resultant solution was adjusted to 30 µl with water, heated at 60° C. for 60 minutes, and diluted to 500 µl with 1× hybridization buffer.

Adduct Protection

In a 12×75 mm tube (Sarstedt) was added 30 µl of borate buffer (30 mM borate (pH 8.8), 1% Triton X100) and 3 to 5 µl of probe or hybrid (200,000–300,000 RLU). To this solution was added 10 µl of 0.1M sodium sulfite or 0.1M sodium metabisulfite. The solution was then vortexed and allowed to sit at room temperature for different amounts of time. Chemiluminescence of the resultant solution was measured by injection of Detect I followed 0.5–2 seconds later by injection of Detect II. Light emission was integrated over a 5-second period.

Results

When attached to either a probe or hybrid, acridinium ester having unsubstituted acridinium rings (AE, o-AE, naphthyl-AE, o-Me-Cin-AE, o-diMe-AE, and o-diBr-AE) formed adducts with sodium sulfite and sodium metabisulfite at about the same rate (within a factor of ten). In contrast, 1-Me-AE and 2,7-di-Me-AE formed adducts more than ten time slower than the unsubstituted acridinium ester derivatives. The lower adduct formation rate by these methylated derivatives can be explained by the electron donating properties of methyl groups which can reduce the positive change at the C-9 position of acridinium ester thereby reducing adduct formation rates.

The results of these experiments are shown in Table I.

TABLE I

| Condition | Compound | Probe $t_{1/2}$ (sec) | Hybrid $t_{1/2}$ (sec) | DA |
|---|---|---|---|---|
| Sodium sulfite | AE | 1.8 | 54 | 30 |
| (10 mM) 30 mM | o-AE | ≦1.1 | 23.8 | 21.6 |
| Borate (pH 8.8 ), | o-diMe-AE | ≦1.5 | 60 | ≧40 |
| 1% TX100 | Naphthyl-AE | 2.3 | 11.8 | 5.1 |
|  | o-Me-Cin-AE | 4.6 | 73 | 15.9 |
|  | 1-Me-AE | 17.9 | — | — |
|  | 2,7di-Me-AE | >77 | — | — |
| Sodium | AE | 3.3 | 107 | 32.4 |
| metabisulfite | o-AE | 2.7 | 64.6 | 24 |
| (10 mM) 30 mM | o-diMe-AE | — | — | — |
| Borate (pH 8.8) | Naphthyl-AE | 2.7 | 46.2 | 17.1 |
|  | o-Me-Cin-AE | 8.3 | — | — |
|  | 1-Me-AE | 18.5 | — | — |
|  | 2,7-diMe-AE | >98 | — | — |
| Sodium Sulfite | AE | 2 | — | — |
| (10 mM) | o-diBr-AE | 4 | — | — |
| 30 mM Borate (pH 8.8) | 2,7-diMe-AE | 49 | — | — |
| 1% TX100 |  |  |  |  |
| Sodium Sulfite | AE | — | 22 | — |

TABLE I-continued

| Condition | Compound | Probe $t_{1/2}$ (sec) | Hybrid $t_{1/2}$ (sec) | DA |
|---|---|---|---|---|
| (15 mM) | o-diBr-AE | — | 8 | — |
| 30 mM Borate (pH 8.8) 1.5% TX100 | 2,7-diMe-AE | — | 444 | — |

DA refers to differential label alteration of signal production for the adduct protection assay.

Thus, the label's structure affects its ability to form an adduct. For example, for a label attached to a probe or hybrid, the rate of adduct formation by o-diBr-AE is 24 and 45 times faster, respectively, than the rate of adduct formation by 2,7-diMe-AE attached to the same probe or hybrid.

EXAMPLE 4

Detection of a Single Base Mismatch

This example illustrates the ability of the adduct protection assay to detect single base pair mismatches. A probe was hybridized to three different target sequences termed TW (wild type target), TM1 (mismatched target one), and TM2 (mismatched target two). Hybridization of the probe to TW yields a hybrid with no mismatches, hybridization of the probe to TM1 yields a hybrid with one mismatch, and hybridization of the probe to TM2 yields a hybrid with two adjacent mismatches.

The adduct formation rate of the probe hybridized with TW, TM1, and TM2 were measured. For comparison purposes, the hydrolysis rates for each probe and target were also determined using alkali solution in a hydrolytic assay.

Probe and Target Sequences

The following probe and target sequences were used in this example (where * indicates the position of the acridinium ester label):

AE Probe

SEQ. ID. No. 7: 5'-CGTTACTCGG ATG*GCCCAAA TATCGCCAC

Wild Type Target (TW)

SEQ. ID. No. 8: 5'-GTGGCGATAT TTGGGC*CATC CGAGTAACG

Mutant Target 1 (TM1)

SEQ. ID. No. 9: 5'-GTGGCGATAT TTGGGG*CATC CGAGTAACG

Mutant Target 2 (TM2)

SEQ. ID. No. 10: 5'-GTGGCGATAT TTGGGC*GATC CGAGTAACG

Hybridization

To 60 μL of hybridization buffer (100 mM lithium succinate (pH 5.2), 8.5% lithium lauryl sulfate, 1.5 mM EDTA, 1.5 mM EGTA) was added 2.5 pmol of target and 0.05 pmol of probe. The resultant solution was heated at 60° C. for 30 minutes and then diluted into 500 μl of 50 mM lithium succinate (pH 5.2), and 250 mM lithium chloride.

Adduct Protection

In a 12×75 mm tube (Sarstedt) was added 100 μl of borate buffer (60 mM borate (pH 8.8), 2% (v/v) TX100) and 10 μl of probe or hybrid. To this solution was added 100 μl of 20 mM sodium sulfite. The solution was then vortexed and allowed to sit at room temperature for different amounts of time. Chemiluminescence of the resultant solution was measured by injection of Detect I followed 0.5 seconds later by injection of Detect II. Light emission was integrated over a 5-second period of time.

Hydrolysis

In a 12×75 mm tube (Sarstedt) was added 100 μl of borate buffer (190 mM sodium tetraborate (pH 7.6), 6.9% (v/v) TX-100, 0.02% fish gelatin (Fisher)) and 10 μl of probe or hybrid. The resultant solution was heated at 60° C. and at various times sample was removed and added to 200 μl of 0.4N HCl containing 0.1% (v/v) $H_2O_2$. Chemiluminescence of the resultant solution was measured by injection of Detect II and light emission was integrated over a 5-second period of time.

Results

The results are shown in Table II.

TABLE II

| | APA | | HA | |
|---|---|---|---|---|
| Hybrid | Probe $t_{1/2}$ (sec) | Hybrid $t_{1/2}$ (sec) | Probe $t_{1/2}$ (min) | Hybrid $t_{1/2}$ (min) |
| P + TW | 3.4 | 34.9 | 0.68 | 18.7 |
| P + TM1 | 3.4 | 58.9 | 0.68 | 1.91 |
| P + TM2 | 3.4 | 13.4 | 0.68 | 3.06 |

"P" refers to probe. "APA" refers to adduct protection assay. "HA" refers to hydrolysis assay.

In the hydrolysis assay, mismatched hybrids hydrolyzed faster than the same hybrid lacking a mismatch, and a single base pair mismatch in the assay significantly reduced signal production from the mismatched hybrid.

The effect of a mismatch in the adduct protection assay differs markedly from the effect of a mismatch in the hydrolysis assay. In contrast to the results obtained for the hydrolysis assay, a single mismatch can result in greater or lesser discrimination between label present on bound and unbound probes in the adduct protection assay. Thus, the effect of a mismatch on the adduct protection assay while reproducible for a particular mismatched probe:target hybrid, can vary for different probe target hybrids (i.e., may increase or decrease protection).

Table II also illustrates the difference in alteration of signal production rates for the adduct protection assay and the hydrolysis assay. In Table II the rate of differential alteration of signal production for the adduction protection assay is measured in seconds, while the hydrolysis alteration of signal production rate is measured in minutes. Overall, the alteration of signal production rate was about 12 to 32 times faster in the adduct protection assay, compared to the hydrolysis assay.

EXAMPLE 5

Different Nucleic Acid Structures

The relationship between adduct formation rates and the type of nucleic acid (RNA or DNA) present in the probe or target is summarized in this example. In these experiments, a small RNA or DNA AE-labelled probe was hybridized to a small complementary RNA or DNA target or to a large ribosomal RNA target. For comparison purposes, the hydrolysis rates of each probe and the resulting hybrid were also determined. Unless otherwise stated the assays were carried out as described in Example 3, using the following oligonucleotide:

(I) Probes

SEQ. ID. No. 5, DNA probe labelled with acridinium ester at the 16/17 position; and SEQ. ID. No. 11: GCUCGUUGCG GGACUU*AACC CAACAU, where * indicates the position of the acridinium ester label.

(II) Targets

SEQ. ID. No. 6 (DNA target); and

SEQ. ID. No. 12 (RNA target); 5'-AUGUUGGGUUAAGUCCCGCA ACGAGC.

Hybridization to rRNA Target

To 15 µl of 2× hybridization buffer was added 2 µg (1.25 pmol) of *E. coli* rRNA. The resultant solution was adjusted to 30 µl with water and heated at 70° C. for 10 minutes. One-tenth pmol of SEQ. ID. No. 5 probe labelled with acridinium ester at the 16/17 position was then added to the solution. The solution was heated at 60° C. for one hour, cooled to room temperature, and diluted to 500 µl with 1× hybridization buffer.

Results

The results are shown in Table III.

EXAMPLE 6

Label Placement Effects Using an AE-Label

To examine the dependence of adduct formation rates on the location of the acridinium ester linker site, a set of probes containing an acridinium ester linker site at different positions along the probe were prepared. This set of probes were then hybridized to complementary targets and the resulting AE-labelled hybrids and AE-labelled probes reacted with sodium sulfite. For comparison purposes, the hydrolysis rates of the same set of probes and hybrids were measured by a hydrolysis assay. As summarized below, adduct formation rates vary greatly (10-fold) from one base to the next along a hybrid and less (2.6-fold) from one base to the next along a probe. In contrast, the variation of hydrolysis rates along a hybrid or probe are smaller (2-fold and 1.6-fold, respectively)- Thus, the ability of an adduct to discriminate between an AE-labelled probe and an AE-labelled hybrid can be greatly enhanced by varying the position of the AE linker site.

TABLE III

| Probe | Target | Probe $t_{1/2}$ (sec) | Hybrid $t_{1/2}$ (sec) | DA | Probe $t_{1/2}$ (min) | Hybrid $t_{1/2}$ (min) | DH |
|---|---|---|---|---|---|---|---|
| RNA[1] | RNA[3] | ≦.78 | 78.1 | ≧100 | 1.7 | 37.9 | 22.3 |
| RNA[1] | DNA[4] | ≦.78 | 44.5 | ≧57 | 1.7 | 10.8 | 6.35 |
| DNA[2] | RNA[3] | 2.1 | 177.7 | 84 | 1.4 | 46.5 | 34.5 |
| DNA[2] | DNA[4] | 1.4, 2.1 | 20.2, 32.8 | 14,3 15.6 | 1.4 | 17.6 | 13 |
| DNA[2] | rRNA | 1.5 | 73.5 | 48 | 1.4 | 45.1 | 33.2 |

"DA" refers to differential adduct formation rate. "DH" refers to differential hydrolysis rate. DA and DH are both measures of differential alteration ratios. "RNA[1]" refers to a probe of SEQ. ID. No. 11. "DNA[2]" refers to a probe of SEQ. ID. No. 5. "RNA[3]" refers to a target of SEQ. ID. No. 12. "DNA[4]" refers to a target of SEQ. ID. No. 6.

The behavior observed in Table III may be related to the conformation of the different nucleic acid hybrids. DNA/DNA hybrids are in a B conformation, RNA/RNA hybrids are in an A conformation, and nucleic acid hybrids containing one DNA strand and one RNA strand are believed to adopt A-like conformations.

The effect of an RNA target and/or RNA probe on discrimination is different for the adduct protection assay and a hydrolysis assay. In the adduct protection assay discrimination increases when both the target and probe are RNA. In contrast, for the hydrolysis assay the largest amount of discrimination was observed for a DNA probe and RNA target. Moreover, the adduct protection assay provided more discrimination than the hydrolysis assay under the experimental conditions used in the example.

Overall, the A-like conformations exhibited adduct formation rates similar to A conformations. In contrast, the hydrolysis rates of these A-like conformations resemble the hydrolysis rate of a B conformation when the target strand is DNA while they resemble the hydrolysis rate of an A conformation when the target strand is RNA. Thus, adduct formation rates depend upon whether a probe and/or target is DNA or RNA and these rates do not directly correlate with the corresponding hydrolysis rates of labels identically associated with these molecules.

TABLE IV

| | LINKER SITE | | | | | | | |
|---|---|---|---|---|---|---|---|---|
| | 7/8 | 9/10 | 11/12 | 12/13 | 13/14 | 14/15 | 15/16 | 17/18 |
| Probe $t_{1/2}$ (sec) | 1.3 | 2.3 | 1.4 | 1.4 | 3.4 | 2.8 | 1.8 | 2.4 |
| Hybrid $t_{1/2}$ (sec) | 29.4 | 65.3 | 12.1 | 39.2 | 34.9 | 19.9 | 22.7 | 122 |
| DA | 22.6 | 28.4 | 8.6 | 28 | 10.3 | 7.1 | 12.6 | 50.8 |
| Probe $t_{1/2}$ (sec) | 0.63 | 0.68 | 0.9 | 0.96 | 0.68 | 0.7 | 0.76 | 0.99 |
| Hybrid $t_{1/2}$ (sec) | 18.6 | 16.5 | 13.3 | 19.2 | 18.7 | 20.6 | 28 | 21.3 |
| DH | 29.5 | 24.3 | 14.8 | 20 | 27.5 | 29.4 | 36.8 | 21.5 |

The assays were carried out as described in Example 4.

EXAMPLE 7

Performance of Different Signal Altering Ligands

To facilitate detection of an analyte by preferential alteration of signal production from an unbound label, it is important that an adduct-forming compound react strongly with the label. Table V summarizes experiments where various nucleophiles are reacted with an unbound AE-labelled probe.

For each nucleophile, the percentage of probe which did not form an adduct was determined over a range of nucleophile concentration. Compounds containing a free pair of electrons on atoms other than sulfur (sulfate, hypophosphite) did not form strong adducts with acridinium ester.

In contrast, compounds containing sulfur atoms with a free pair of electrons formed strong adducts with acridinium esters (tetrahydrothiophene, propanethiol, sodium sulfite, benzyl mercaptan, sodium hydrosulfite, glycol sulfite, metabisulfite, sodium thiophosphate, and sodium thiosulfate). Only one sulfur containing compound, propyl disulfide, failed to form a strong adduct to acridinium owing to its limited water solubility. In addition to sulfur, compounds containing another group VIb atom (potassium tellurite) or a group VIb atom (meta-arsenite) also formed strong adducts with acridinium ester.

To measure the ability of signal altering ligands to preferentially inhibit unbound AE-labelled probe, equivalent amounts of unbound and bound probe (AE-hybrid) were reacted with different concentrations of each signal altering ligand using the procedures described in Example 1. Discrimination was measured either kinetically by calculating a DA ratio or thermodynamically by calculating the percentage of hybrid and probe which did not form an adduct at equilibrium (% hybrid/% probe). Signal altering ligands which do not discriminate between unbound AE-probe and AE-hybrid exhibit a DA or (% hybrid/% probe) ratio of 1 while those which do discriminate between labels present on unbound and bound probes exhibit ratios greater than 1.

As summarized in Table V, nearly all compounds which formed strong adducts with label present on unbound probe formed adducts more readily with label present on unbound probe than with label present on bound probe. Compounds which did not discriminate contained either a sulfur atom conjugated to an aromatic ring (thiophenol, 5-mercapto-1-methyl tetrazole, or 2-mercaptoimidazole) or a sulfur atom conjugated to a nitrile group (thiocyanate).

TABLE V

| Compound | Concentration (nM) | % Probe at equilibrium | DA | % H/% P at equilibrium |
|---|---|---|---|---|
| Propyldisulfide | 2 | 41 | 13.6 | 2 |
| | 20 | 60, 40 | — | 1.5, 2 |
| | 50 | 40 | — | 2 |
| Sodium sulfate | 20 | — | 4 | — |
| | 200 | 60 | 3 | 1.7 |
| Sodium Hypophosphite | 2 | 65 | — | 1.2 |
| | 200 | 53 | 4 | 1.6 |
| | 500 | 55 | — | — |
| Tetrahydro-thiophene | 2 | 75 | — | — |
| | 20 | 19 | — | 2.5 |
| | 100 | <0.2 | — | 40 |
| Propanethiol | 2 | 4 | — | 21.4 |
| | 20 | 2 | 10 | 20.5 |
| | 200 | <1 | — | <1.7 |
| Sodium Sulfite | 2 | 2 | 5.5 | 21.6 |
| | 20 | 0.4, 0.7 | — | 23.6, 12.7 |
| | 200 | <0.1 | — | 2.9 |
| Benzyl-mercaptan | 0.05 | 2.5 | 47 | 25 |
| | 0.1 | 1.5 | 41.5 | 31 |

TABLE V-continued

| Compound | Concentration (nM) | % Probe at equilibrium | DA | % H/% P at equilibrium |
|---|---|---|---|---|
| | 0.5 | 0.3 | — | 20 |
| | 2 | <0.05 | — | 24 |
| | 10 | <0.05 | — | 30 |
| Sodium Hydrosulfite | 2 | 4 | 5.4 | 10 |
| Glycol Sulfite | 2 | <2.5 | 6.1 | >22 |
| Sodium Metabisulfite | 4 (pH 8.8) | 0.3 | >13.7 | 2.3 |
| | 4 (pH 7.9) | 1 | 79 | — |
| | 20 (pH 8.4) | <0.2 | — | 1 |
| Sodium Thiosulfate | 20 | 42 | — | — |
| | 200 | 3 | — | >8 |
| | 500 | 4 | — | >7 |
| Sodium Thiophosphate | 20 | 1 | — | 81 |
| | 50 | 0.3 | — | 134 |
| | 100 | <1 | — | — |
| | 200 | <1 | — | 1.2 |
| Sodium Meta Arsenite | 20 (pH 9.4) | 40 | — | 2.4 |
| | 100 (pH 10) | <0.3 | — | >170 |
| | 200 (pH 10.3) | <0.3 | — | >10, 20 |
| Potassium Tellurite | 20 | <8 | >4 | >10.2 |
| | 200 | <1 | — | >92 |
| Sodium Thiocyanate | 1 | 70 | — | — |
| | 4 | 55 | — | 1.3 |
| | 20 | 23 | — | 1.3 |
| | 100 | 6 | — | 1.3 |
| | 200 | 3 | — | 1.6 |
| Thiophenol | 0.5 | 56 | — | 1.2 |
| | 1 | 39 | — | 1.2 |
| | 2 | 57 | 1.3 | — |
| | 10 | 0.9 | — | 2 |
| 5-Mercapto-1-Methyl-tetrazol | 1 | 43 | 1 | 1.2 |
| | 2 | 39 | — | 1.1 |
| | 4 | 22 | — | 1 |
| | 20 | 6 | — | 1.1 |
| | 200 | 0.5 | — | 1 |
| 2-Mercapto Imidazole | 0.5 | — | 0.8 | — |
| | 1 | 80 | — | 13 |
| | 4 | 55 | — | 1.2 |
| | 20 | 22 | — | 1.3 |
| | 200 | 0.8 | — | 1 |

EXAMPLE 8

Effect of Sequence on APA

To examine the dependence of adduct formation rates on the sequence of a nucleic acid, DNA probes: SEQ. ID. No. 1 (labelled with AE at the 7/8 position), SEQ. ID. No. 5 (labelled with AE at the 16/17 position), and SEQ. ID. No. 13 (SEQ. ID. No. 13: 5'-CTAAAGCGCT T*TCCACCACA AGAC, where * indicates the position of the acridinium ester label) were hybridized to complementary DNA targets (SEQ. ID. No. 2, SEQ. ID. No. 6, or SEQ. ID. No. 14 (5'-GTCTTGTGGT GGAAAGCGCT TTAG) and reacted with sodium sulfite.

Method A

Method A was performed as described in Example 3.

Method B

Method B was performed as follows:
Hybridization

To 15 μl of 2× hybridization buffer was added 1 pmol of AE-labelled probe (7×10$^7$ RLU/pmol) and 4 pmol of target. The resultant solution was adjusted to 30 μl with water, heated at 60° C. for 30 minutes, and diluted to 500 μl with 1× hybridization buffer.

Adduct Protection

In a 12×75 mm tube (Sarstedt) was added 2 μl of AE-labelled probe or hybrid (400.000 RLU). To this solution was added 100 μl of adduct forming buffer (10 mM sodium sulfite, 30 mM borate buffer (pH 8.7), and 1.5% Triton TX100). The solution was then vortexed and allowed to sit at room temperature for different amounts of time. Chemiluminescence of the resultant solution was measured by injection of Detect I followed 0.5–2 seconds later by injection of Detect II. Light emission was integrated over a 5-second period.

Results

The results of these experiments are shown in Table VI.

TABLE VI

| Condition | Probe (SEQ. ID. No.) | Target (SEQ. ID. No.) | Probe $t_{1/2}$ (sec) | Hybrid $t_{1/2}$ (sec) | DA |
|---|---|---|---|---|---|
| A. 10 mM sodium sulfite, 30 mM borate pH 8.8, 1% TX100 | 13 | 14 | <0.64 | 9.1 | >14.2 |
|  | 5 | 6 | 1.75 | 26.5 | 15 |
| B. 10 mM sodium sulfite, 30 mM borate pH 8.7 1.5% TX100 | 5 | 6 | 2.1 | 31 | 14.7 |
|  | 1 | 2 | <0.9 | 15 | >15.5 |

SEQ. ID. No. 1 was labelled with AE at the 7/8 position, SEQ. ID. No. 5 was labelled with AE at the 16/17 position), and SEQ. ID. No. 13 was labelled with AE at the 11/12 position.

The three different AE-labelled probe sequences as well as their corresponding hybrids react with sodium sulfite to different degrees. Probe SEQ. ID. No. 5 reacts more slowly than probe SEQ. ID. No. 1, which reacts in turn more slowly than probe SEQ. ID. No. 13. Thus, adduct formation rates is effected by the sequence of the AE-labelled probe as well as the sequence of the corresponding hybrid.

Other embodiments are within the following claims. Thus, while several embodiments have been shown and described, various modifications may be made, without departing from the spirit and scope of the present invention.

We claim:

1. A method of assaying for an analyte in a sample comprising the steps of:
   a) exposing said sample to a labelled binding partner comprising an analyte binding region and a label;
   b) treating said sample exposed to said labelled binding partner with a signal altering ligand that preferentially forms a reversible adduct with label present on said labelled binding partner when said labelled binding partner is not bound to said analyte compared to when said labelled binding partner is bound to said analyte, such that said signal altering ligand alters signal production from said labelled binding partner not bound to said analyte to a greater extent than it alters signal production from said labelled binding partner bound to said analyte; and
   c) detecting signal produced from label which was not altered as an indication of the presence or amount of said analyte in said sample.

2. The method of claim 1, wherein said binding partner is a nucleic acid probe and said analyte is a target nucleic acid sequence.

3. The method of claim 1, wherein said assay is performed without separating binding partner bound to said analyte from binding partner not bound to said analyte.

4. The method of claim 1, further comprising separating binding partner bound to said analyte from binding partner not bound to said analyte prior to said step (c).

5. The method of claim 1, wherein said steps (b) and (c) are carried out at an essentially constant temperature.

6. The method of claim 5, wherein said assay is carried out at about room temperature.

7. The method of claim 1, wherein light absorbance is detected in said step (c).

8. The method of claim 1, wherein light emission is detected in said step (c).

9. The method of claim 1, wherein said ligand comprises either a sulfur atom with a free electron pair, a tellurite atom with a free electron pair, or an arsenite atom with a free electron pair, wherein said sulfur atom, said tellurite atom, or said arsenite atom is not conjugated to an aromatic ring or nitrile.

10. The method of claim 1, wherein said ligand is selected from the group consisting of tetrahydrothiopene, propanethiol, benzylmercaptan, sulfite, glycol sulfite, hydrosulfite, metabisulfite, thiosulfate, thiophosphate, metaarsenite, tellurite, arsenite and thiocyanate.

11. The method of claim 8, wherein said ligand comprises either a sulfur atom with a free electron pair, a tellurite atom with a free electron pair, or an arsenite atom with a free electron pair, wherein said sulfur atom, said tellurite atom, or said arsenite atom is not conjugated to an aromatic ring or nitrile.

12. The method of claim 8, wherein said ligand is selected from the group consisting of tetrahydrothiopene, propanethiol, benzylmercaptan, sulfite, glycol sulfite, hydrosulfite, metabisulfite, thiosulfate, thiophosphate, metaarsenite, tellurite, arsenite and thiocyanate.

13. The method of claim 1, wherein said label has the chemical structure:

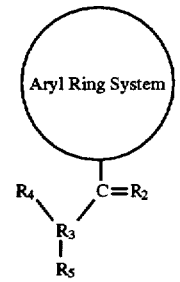

wherein the aryl ring system comprises one to four cyclic groups and one of said groups is joined to linking carbon "c."

$R_2$ is selected from the group consisting of S, O, and NH;

$R_3$ is selected from the group consisting of O, N, S, halogen, substituted phosphorous, substituted sulfur, substituted boron, and substituted arsenic;

$R_4$ is selected from the group consisting of alkyl, alkenyl, aryl, alkoxy, aryloxy, or is absent when $R_3$ is halogen; and $R_5$ is nothing unless $R_3$ is N, if $R_3$ is N then $R_5$ is selected from the group consisting of hydrogen, alkyl, alkenyl, aryl, alkoxy, and aryloxy.

14. The method of claim 13, wherein said aryl system is positively charged.

15. The method of claim 14, wherein said aryl ring system has one to four cyclic groups;

said $R_3$ is selected from the group consisting of O, N, and S, said $R_4$ is aryl, and said $R_5$ is nothing.

16. The method of claim 15, wherein said label has the structure:

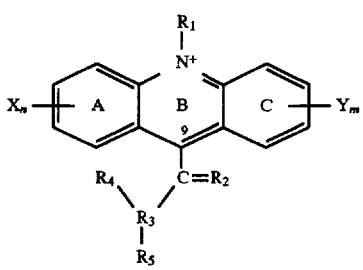

wherein $R_1$ is selected from the group consisting of H, alkyl, alkenyl, alkynyl, and aryl;

n is either 0, 1, 2, 3, or 4;

m is either 0, 1, 2, 3, or 4;

each X is independently selected from the group consisting of alkyl, alkenyl, alkynyl, aryl, amino, substituted amino, carboxy, hydroxy, alkoxy, nitro, sulfonyl, halogen, thiol, amido, acetyl, substituted acetyl, and aryloxy; and each Y is independently selected from the group consisting of alkyl, alkenyl, alkynyl, aryl, amino, substituted amino, carboxy, hydroxy, alkoxy, nitro, sulfonyl, halogen, thiol, amido, acetyl, substituted acetyl, and aryloxy.

17. The method of claim 16, wherein said n is either 0, 1 or 2;

said m is either 0, 1, or 2;

said $R_3$ is O, said $R_4$ is aryl, and said $R_5$ is nothing.

18. The method of claim 17, wherein each of said X is independently either alkyl or alkoxy;

each of said Y is independently either alkyl or alkoxy; and said $R_4$ is an optionally substituted phenyl.

19. The method of claim 18, wherein said $R_4$ is selected from the group consisting of ortho-methyl-cinnamate-phenyl, ortho-dimethyl-phenyl, ortho-dibromophenyl and unsubstituted phenyl.

20. A method for assaying for a nucleic acid target region in a sample comprising the steps of:

a) exposing said sample to a nucleic acid probe comprising an oligonucleotide having a nucleic acid sequence able to bind to said target region and a label;

b) treating said sample exposed to said probe with a signal altering ligand that preferentially forms a reversible adduct with label present on said probe when said probe is not bound to said target region compared to when said probe is bound to said target region, such that said signal altering ligand alters signal production from said probe not bound to said target region to a greater extent than it alters signal production from said probe bound to said target region; and c) detecting signal produced from label which was not altered as an indication of the presence or amount of said target region in said sample.

21. The method of claim 20, wherein said target region is RNA.

22. The method of claim 20, wherein said assay is performed without separating probe bound to said target region from probe not bound to said target region.

23. The method of claim 20, further comprising separating probe bound to said target region from probe not bound to said target region prior to said step (c).

24. The method of claim 20, wherein said steps (b) and (c) are carried out at an essentially constant temperature.

25. The method of claim 24, wherein said assay is carried out at about room temperature.

26. The method of claim 20, wherein light absorbance is detected in said step (c).

27. The method of claim 20, wherein light emission is detected in said step (c).

28. The method of claim 27, wherein said label has the chemical structure:

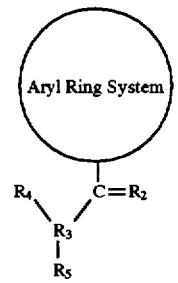

wherein said aryl ring system comprises one to four cyclic groups, one of said groups being an aryl joined to linking carbon "c,"

$R_2$ is selected from the group consisting of S, O, and NH;

$R_3$ is selected from the group consisting of O, N, S, halogen, substituted phosphorous, substituted sulfur, substituted boron, and substituted arsenic;

$R_4$ is selected from the group consisting of alkyl, alkenyl, aryl, alkoxy, and aryloxy, or is absent when $R_3$ is halogen; and $R_5$ is nothing unless $R_3$ is N, if $R_3$ is N then $R_5$ is selected from the group consisting of hydrogen, alkyl, alkenyl, aryl, alkoxy, and aryloxy.

29. The method of claim 28, wherein said aryl system is positively charged.

30. The method of claim 29, wherein said aryl ring system has one to four cyclic groups;

said $R_3$ is selected from the group consisting of O, N, and S, said $R_4$ is aryl, and said $R_5$ is nothing.

31. The method of claim 30, wherein said label has the structure:

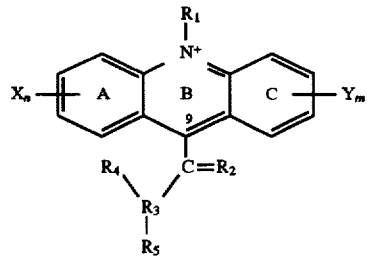

wherein $R_1$ is selected from the group consisting of H, alkyl, alkenyl, alkynyl, and aryl;

n is either 0, 1, 2, 3, or 4;

m is either 0, 1, 2, 3, or 4;

each X is independently selected from the group consisting of alkyl, alkenyl, alkynyl, aryl, amino, substituted amino, carboxy, hydroxy, alkoxy, nitro, sulfonyl, halogen, thiol, amido, acetyl, substituted acetyl, and aryloxy; and each Y is independently selected from the group consisting of alkyl, alkenyl, alkynyl, aryl, amino, substituted amino, carboxy, hydroxy, alkoxy, nitro, sulfonyl, halogen, thiol, amido, acetyl, substituted acetyl, and aryloxy.

32. The method of claim 31, wherein said n is either 0, 1 or 2;

said m is either 0, 1, or 2;

said $R_3$ is O, said $R_4$ is aryl, and said $R_5$ is nothing.

33. The method of claim 32, wherein each of said X is independently either alkyl or alkoxy;

each of said Y is independently either alkyl or alkoxy; and said $R_4$ is an optionally substituted phenyl.

34. The method of claim 33, wherein said $R_4$ is selected from the group consisting of ortho-methyl-cinnamate-phenyl, ortho-dimethyl-phenyl, ortho-dibromo-phenyl and unsubstituted phenyl.

35. The method of claim 20, wherein said ligand is selected from the group consisting of tetrahydrothiopene, propanethiol, benzylmercaptan, sulfite, glycol sulfite, hydrosulfite, metabisulfite, thiosulfate, thiophosphate, metaarsenite, tellurite, arsenite and thiocyanate.

36. The method of claim 20, wherein said ligand comprises either a sulfur atom with a free electron pair, a tellurite atom with a free electron pair, or an arsenite atom with a free electron pair, wherein said sulfur atom, said tellurite atom, or said arsenite atom is not conjugated to an aromatic ring or nitrile.

* * * * *